(12) United States Patent
Dean et al.

(10) Patent No.: US 6,849,223 B2
(45) Date of Patent: Feb. 1, 2005

(54) FABRICATION OF A POLYMERIC PROSTHETIC IMPLANT

(75) Inventors: David Dean, Shaker Heights, OH (US); Malcolm Cooke, Richfield, OH (US)

(73) Assignee: Case Western Reserve University, Cleveland, OH (US)

( * ) Notice: Subject to any disclaimer, the term of this patent is extended or adjusted under 35 U.S.C. 154(b) by 372 days.

(21) Appl. No.: 10/127,019

(22) Filed: Apr. 19, 2002

(65) Prior Publication Data

US 2002/0171178 A1 Nov. 21, 2002

Related U.S. Application Data

(60) Provisional application No. 60/284,803, filed on Apr. 19, 2001.

(51) Int. Cl.[7] .............................................. B29C 35/08
(52) U.S. Cl. ........................ 264/400; 264/401; 264/482; 264/494; 156/272.8; 156/273.5; 156/275.5; 156/298; 156/303.1; 156/379.8
(58) Field of Search ................................. 264/400, 401, 264/482, 494; 156/272.8, 273.5, 275.5, 298, 303.1, 379.8

(56) References Cited

U.S. PATENT DOCUMENTS

| | | | |
|---|---|---|---|
| 4,996,010 A | * | 2/1991 | Modrek ..................... 264/401 |
| 6,071,982 A | | 6/2000 | Wise et al. |
| 6,124,373 A | * | 9/2000 | Peter et al. .................. 523/116 |
| 6,261,493 B1 | | 7/2001 | Gaylo et al. |
| 2004/0054372 A1 | * | 3/2004 | Corden et al. ................ 606/77 |

OTHER PUBLICATIONS

International Search Report dated Aug. 30, 2002.

* cited by examiner

*Primary Examiner*—Stefan Staicovici
(74) *Attorney, Agent, or Firm*—Calfee, Halter & Griswold LLP

(57) ABSTRACT

Processes for fabricating a customized, three-dimensional, bioerodable, polymeric prosthetic implant are provided. In a highly preferred embodiment, the prosthetic implant has a porous network. The method employs a sterolithography instrument, a solution comprising chains of one or more photocurable, bioerodable polymers and a photoinitiator, and a three-dimensional CAD image. In a highly preferred embodiment, the solution comprises poly (propylene) fumarate (PPF) and a solvent for controlling the viscosity of the solution. During the fabrication process, the solution is placed in a container in the stereolithography instrument. The container also holds a movable build platen for supporting each of the covalently bonded layers of the polymeric prosthetic implant that are formed when successive layers of the solution are exposed to UV light energy. The UV light energy is imparted to selected portions of each layer of the solution to produce a pattern of cross-linked and non-cross-linked polymeric regions corresponding to a cross-sectional image of the three-dimensional CAD image.

15 Claims, 5 Drawing Sheets

FABRICATION OF A POLYMERIC PROSTHETIC IMPLANT

REFERENCE TO RELATED APPLICATION

This application claims priority to U.S. Provisional Application No. 60/284,803 filed on Apr. 19, 2001.

STATEMENT OF GOVERNMENT SUPPORT

This invention is supported, at least in part, by Grant No. DE 13740 from the National Institutes of Health, U.S. Public Health Service. The U.S. government has certain rights in this invention.

BACKGROUND OF THE INVENTION

Large skeletal defects frequently arise following reconstructive surgery for trauma, cancer resection, infection and congenital deformity. The standard clinical treatment for these defects is the transplantation of a bone graft derived from the patient (autograft) into the defect site. Although an autograft, typically, does not cause an immune response, it is associated with several disadvantages including donor site morbidity and limited availability. Furthermore, it is possible that an autograft will not successfully vascularize in the new site, leading to its resorption and/or infection of the graft site.

Other treatments may be used to replace the defect. These include implantation of a bone cement (calcium phosphate, acrylic [e.g., PMMA], or plastic [e.g., polyethylene]) or a metal prosthetic. Unfortunately, the long term persistence of these materials can lead to complications at and surrounding the defect site. For example, because such materials may have a different modulus and strength than the surrounding tissue, implantation of prosthetic devices made from such materials into the defect site can lead to damage of the surrounding tissues. Moreover, prosthetic devices made from these materials do not (a) revascularize or allow for tissue regeneration in the defect site, (b) integrate with the existing host bone, or (c) undergo subsequent remodeling in response to evolving mechanical (i.e., ambulatory loading or protection of internal organs) needs. This leads to problems with protective strength and aesthetics as the host bone remodels around the implanted prosthetic. The problems are magnified by the post-surgical need to protect the brain or other internal organs covered by prosthetic from infection and trauma during the healing process.

The inadequacies of the current prosthetics have led to an investigation of prosthetics that act as porous scaffold for attachment and proliferation of tissue progenitor (e.g., bone progenitor) cells. It has been proposed that such scaffolds be made from a biodegradeable polymer that slowly degrades away, eventually leaving a defect site that has been repaired by the cells which migrate into and attach to the scaffold. Prior to its degradation, the scaffold serves not only to provide a surface for attachment of the progenitor bone cells, but also to allow in nutrients and to support any biomechanical functions (ambulatory loading or protection).

Polymeric scaffolds have been fabricated by a chemical cross-linking process or, more recently, by photocrosslinking the liquid polymeric material in a transparent mold. Molds do not facilitate the formation of internal spaces such as pores. To overcome this deficiency, investigators have tried to stir salt crystals into the polymer and later leach it out with water. The salt crystal space is left as a pore, but the surface texture and arrangement of pores is not homogenous and geometrically may not be conducive to cell attachment, proliferation, or maturation, as well as vascular ingrowth.

Accordingly, it is desirable to have new methods for fabricating biodegradable polymeric prosthetics for treating critical size bone defects. It is also desirable to have a method which provides a prosthetic that not only maintains its shape and protective strength during the healing process but also encourages bone ingrowth and incorporation of the prosthetic with the host bone. It is also desirable to have a method for fabricating a prosthetic which comprises a polymer that, when prosthetic implanted into a defect site, does not degrade into by-products that have serious adverse affects on the cells and tissues in contact with the prosthetic.

SUMMARY OF THE INVENTION

The present invention provides a method of fabricating a customized three-dimensional prosthetic implant for use in repairing a critical size tissue defect, particularly a critical size bone defect in a patient. As used herein the term "critical size bone defect" refers to a bone defect that the patient cannot heal without assistance. As used herein the term "customized" refers to a prosthetic prosthetic implant whose size and shape dimensionally matches the bone defect site in the patient. Preferably, such prosthetic comprises a series of interconnecting pores that provide at least one channel, more preferably a network of interconnecting channels, leading from the exterior surface of the prosthetic implant to a predetermined location in the interior of the prosthetic implant. The pores and channels are defined by surfaces which provide points of bone or vascular progenitor cells.

The present method comprise the following steps: providing a solution comprising chains of a photopolymerizable, bioerodable, liquid polymeric materials (referred to hereinafter as a "primary polymer") and a photoinitiator for promoting photocrosslinking of the primary polymer; providing a stereolithography instrument comprising a UV laser for activating the photoinitiator and photocrosslinking the primary polymer; providing a CAD image of the desired three-dimensional prosthetic prosthetic implant, wherein said CAD image is readable by the stereolithography instrument; depositing the solution in successive layers on a build platen in the stereolithography instrument; and photocrosslinking the primary polymer in each of the successive layers according to corresponding cross-sectional patterns derived from the CAD image. The fabrication method may further comprise an earlier step of scanning a bone to be duplicated to provide data and converting the data into the three dimensional CAD image. In one highly preferred embodiment of the present method, the primary polymer is a poly (propylene fumarate) (hereinafter "PPF"), and the solution further comprises a solvent for reducing the viscosity of the PPF liquid. Optionally, the solution further comprises chains of one or more additional photopolymerizable polymers (referred to hereinafter as the "secondary polymer") for preparing a composite prosthetic implant.

The present invention also provides an prosthetic implant prepared in accordance with the present method. Such prosthetic implant comprises solid regions comprising the photocrosslinked primary polymer and has a network of interconnecting pores and channels leading from the exterior surface to an interior location in the prosthetic prosthetic implant. Preferably, the diameter of the pores and channels is from about 100 microns to about 1000 microns. In certain embodiments, the prosthetic implant is a composite prosthetic prosthetic implant wherein a portion or all of the solid regions of the prosthetic prosthetic implant comprise a photcrosslinked primary polymer and a photocrosslinked secondary polymer. In other embodiments, the prosthetic prosthetic implant is a composite prosthetic prosthetic implant wherein a first group of solid regions in the prosthetic implant comprise the photo-cross-linked primary polymer and a second group of solid regions in the prosthetic implant comprise a photocrosslinked secondary polymer. The prosthetic implant may also comprise bioactive molecules.

DETAILED DESCRIPTION OF THE INVENTION

Figure 1:
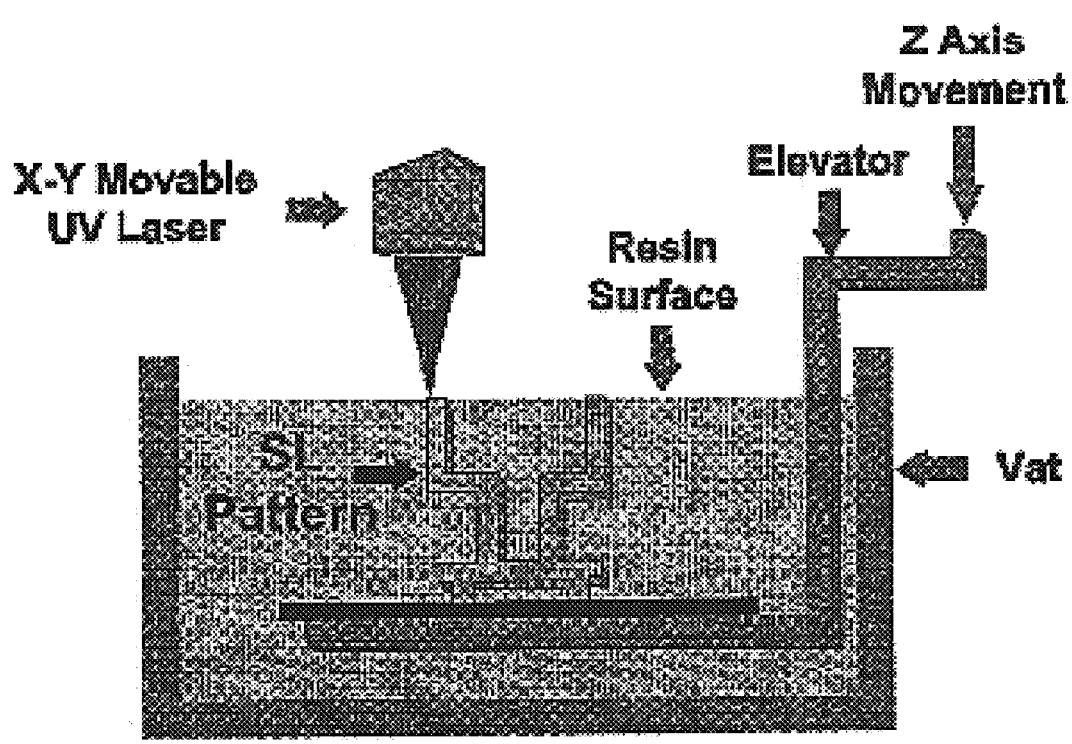
FIG. 1: Laser Curing Device (3D Systems 250/40 SLA): A CAD file is converted into slice data. A high resolution laser beam moves over a vat of resin. The resin is hardened to a prescribed depth of 0.1 mm (100 microns), one slice at a time. Elevator platform moves down 0.1 mm after each layer is polymerised. Adjacent layers polymerise to one another, held in registration by supports bound to the elevator (build) platen. (Image Copyright 3D Systems, Valencia, Calif.)

The present invention provides a process for fabricating a customized, three-dimensional, bioresorbable, polymeric prosthetic implant, particularly a bone prosthetic implant. In a highly preferred embodiment, the prosthetic implant has a porous network. The method employs a sterolithography instrument, a solution comprising chains of one or more photocurable, bioerodable polymers and a photoinitiator, and a three-dimensional CAD image. In a highly preferred embodiment, the solution comprises poly (propylene) fumarate (PPF) and a solvent for controlling the viscosity of the solution. Optionally, the solution comprises chains of a second photocurable polymer or chains of a second photocurable polymer and a second photoinitiator. Preferably, the solution further comprises bioactive molecules that promote attachment, proliferation, and/or differentiation of vascular and/or bone progenitor cells. During the fabrication process, the solution is placed in a container in the stereolithography instrument. The container also holds a movable build platen for supporting each of the covalently bonded layers of the polymeric prosthetic implant that are formed when successive layers of the solution are exposed to UV light energy. The UV light energy is imparted to selected portions of each layer of the solution to produce a pattern of cross-linked and non-cross-linked polymeric regions corresponding to a cross-sectional image of the three dimensional CAD image. At some point in the process the non-cross-linked polymeric resin in the prosthetic implant is washed away Definitions The singular forms "a," "an" and "the" are used herein to include the plural unless the content clearly dictates otherwise. Thus, for example, reference to "a PPF polymer" includes more than one such polymer, reference to "a layer" includes more than one layer, and the like.

The term "bioerodable" as used herein refers to a polymer whose solid form degrades by surface erosion or bioerosion rather than bulk degradation. Two distinct types of degradation can occur with implanted solid polymers. One type of degradation is bulk degradation, in which the polymer degrades in a fairly uniform manner throughout the matrix. The prevailing mechanism of bulk degradation is hydrolysis of the hydrolytically unstable polymer backbone. First, water penetrates the bulk of the solid polymeric implant, preferentially attacking chemical bonds in the amorphous phase and converting long polymer chains into shorter water-soluble fragments. This results, initially, in a reduction in molecular weight ($M_n$) without an immediate change in physical properties. Once the polymeric implant begins to fragment, a reduction in mechanical strength of the polymer occurs. Next, enzymatic attack and metabolization of the fragments occurs. At this point, the rate at which the water penetrates the implant exceeds that at which the polymer is converted into water-soluble materials, and the remaining implant comes apart.

The second type of degradation is surface erosion, which is also called bioerosion. Bioerosion occurs when the rate at which water penetrates the prosthetic implant is slower than the rate of the conversion of the polymer into water-soluble materials. Bioerosion results in a thinning of the prosthetic implant over time, though the prosthetic implant's bulk integrity is maintained.

PPF is a bioerodable polymer. PLA, PGA, and PLGA may degrade in bulk and, therefore, for the purposes of the present invention, are not considered to be bioerodable polymers.

The term "CAD" is used herein in its broadest sense to include all manner of computer aided design systems, including pure CAD systems, CAD/CAM systems, and the like, provided that such systems are used at least in part to develop or process a model of a three-dimensional polymeric bone prosthetic implant.

The term "three-dimensional polymeric prosthetic implant" is used herein to mean any polymeric prosthetic implant that substantially retains its intended function and shape when removed from an external support.

The term "cross-sectional pattern" is used herein to mean a representation of a cross-section of the prosthetic implant being built. Generally speaking, the cross-sectional pattern will be a complete vertical cross-section, because most prosthetic implants are contemplated to be produced one complete layer at a time, in a vertical, stepwise fashion.

The terms "photocrosslink" and "photocure" as used herein are interchangeable and refer to a process that is initiated by exposure of a polymer to UV radiation in the presence of a photoinitiator, and that results in the formation of chemical links between molecular chains of the polymer. In accordance with the present methods, the bioresorbable polymers which are used to prepare the present prosthetic implants are uncrosslinked, or uncured, prior to exposure to activating UV radiation. In accordance with the present methods, the final prosthetic implant comprises select and predetermined solid regions of a photocrosslinked or photocured polymer, preferably a photocrosslinked or photocured PPF polymer.

The term "successive layer" as used herein refers to the layer of solution that is sequentially deposited on the build platen or the previous photocrosslinked layer of the polymeric prosthetic implant during the stereolithographic procedure. In accordance with the present invention, there is inter layer bonding between each of the photocrosslinked layers of the polymeric prosthetic implant.

"Ultraviolet or UV radiation" is radiation in the region of the electromagnetic spectrum including wave-lengths from 100 to 3900 angstroms.

In step 1 of the present method, a computer representation or three-dimensional "image" of the prosthetic implant to be formed, including its internal network of pores is generated using a CAD/CAM software system. The software then preferably generates an STL file for use in a sterolithography instrument. The STL file is converted into "slice" data corresponding to vertical cross-sectional patterns (X-Y slices of Z thickness) of the desired prosthetic implant, a process termed stereolithography (SLA).

In step 2, a layer of the solution is applied either to the work surface of the build platen or to a previous photocrosslinked polymeric layer. Thereafter, the layer is leveled to a desired thickness that corresponds to the thickness of the "slice" generated by the computer and the depth of polymerization of the particular laser/initiator/polymer combination used.

In step 3, appropriate slice data from step 1 is fed to a selective photoexposure device, which in turn exposes the layer of solution deposited in step 2 to one or more scanning UV lasers according to the corresponding cross-sectional pattern derived from the three-dimensional CAD image. Appropriate intensity and duration of the exposure is contemplated to be established experimentally. Nevertheless, it may be understood that suitable values for these parameters will vary as a function of numerous factors, including the nature of the photocurable polymers in the solution, the amount and activity of the photoinitiator, and the thickness and transparency of each layer to the radiation. Such exposure is selected to provide a suitable, predetermined degree of cross-linking between the polymeric chains of the photocurable polymer, while still permitting adequate bonding between adjacent layers. Specific exposure parameters are given below, but in general it is contemplated that intensity will correspond to the wavelength at which the photoinitiator in the solution has maximum absorbance.

Variation of the laser intensity or traversal speed can be used to vary the cross-link density within a layer so that the physical properties of the solid polymeric regions can be varied from position to position within the prosthetic implant. Cross-linking density can also be altered by varying the ratio of the photocurable polymer to solvent in the solution and by employing two or more photocurable polymers having different molecular weights and different numbers of cross-linking sites along the polymer chains.

In step 4, the PPF oligomeric and polymeric chains in the solution are photocrosslinked upon exposure to the UV radiation to form a cross-linked region shaped according to the corresponding computer-generated cross-sectional pattern. It is not necessary that such regions be fully cured, as complete curing can be accomplished in a post-SLA UV cure.

In step 5, steps 2 through 4 are repeated to gradually build up the desired prosthetic implant and, preferably, a support structure whose dimensions and locations are also incorporated into the CAD image.

Preferably, during the build up of the prosthetic implant, select cross-linked regions of the layers of the prosthetic implant are offset to form a porous network. After removal from the stereolithography instrument, the prosthetic implant is washed in a bath to remove unpolymerized polymer and excess solvent. Preferably, the prosthetic implant is then exposed to UV radiation to complete cross-linking of the solid polymeric regions and bonding between the solid polymeric layers of the prosthetic implant.

Optionally, step 1 of the method is preceded by a step comprising scanning a bone to be duplicated to produce data and converting such date into the three dimensional CAD image. Suitable bone scanning methods include, but are not limited to, three dimensional CT scanning, MRI, film X-rays, and two-dimensional and three-dimensional ultrasound. Because of its accuracy, the preferred scanning method is CT.

Advantageously, the present methods provide prosthetic implants whose size and shape match the bone defect site geometry. The prosthetic implants made in accordance with the present method also, advantageously, have a network of investing and interconnecting pores whose sizes and location can be precisely controlled during the fabrication process. Moreover, the present methods are a significantly faster means of producing a directly implantable prosthetic which can establish or return the defect site to desired function with acceptable aesthetics.

The present method allows fabrication of prosthetic implants having regions with different degrees of strength and resorption rate. Although the strength and the resorption rate may be uniform across the implant, it is expected that implants with regions that are variously loaded will have a higher degree of strength in some regions than others. In order to regenerate a loaded section, supporting structures will need to be arrayed next to porous spaces allowing bone ingrowth. These supporting structures may be nondegradable, slowly degradable, or relatively quickly degradable dependant on the needs of the defect site.

For optimum performance, tissue must grow into the prosthetic implant from nearby host tissue, so good fit is highly desirable in areas where rapid host tissue ingrowth is a priority. This present fabrication method provides significantly higher resolution control over the geometry of prosthetic implants that are produced. The higher resolution of the resulting prosthetic implant allows for complex design of internal geometries, including porous spaces, with can promote tissue ingrowth.

The present method is useful for fabricating prosthetic implants from polymers that are resorptive and from polymers that are not resorptive. Accordingly, the present fabrication method allows the formation of prosthetics with varying strength and degradation properties, by permitting the manufacturer to control the molecular weight and cross-linking density of the polymer used to form the prosthetic and/or to control the array and percentage of open space. The present fabrication method also allows the design of surface textures which will influence cell attachment properties. Finally, the present method allows the design of internal spaces in configurations which promote maturation of tissues, such as the lamellar arrangement of mature lamellar bone. In addition to polymer, other materials (e.g., signaling molecules, cell attachment molecules) can be either incorporated into the polymer directly (i.e., part of the polymer chain) or in solution with the non-crosslinked polymer so that they become incorporated into the prosthetic implant during photo-crosslinking of the polymer chains.

Stereolithography

Stereolithography (SL) is a sequential layering process. See, Jacobs, "Rapid Prototyping and Manufacturing-Fundamentals of Stereolithography," (SME, Dearborn, Mich. 1992). SLA is based on the use of a focused ultraviolet (UV) laser which is vector scanned over the top of a solution comprising chains of a photopolymerizable or photocurable polymer. The UV laser causes chains of the photocurable polymer to polymerize where the laser beam strikes the surface of the solution and to a certain depth below the surface of the solution. The depth of polymerization depends on the power of the laser light. This results in the creation of a first solid polymeric layer at and just below the surface. The solid polymeric layer is then lowered into the solution and the laser generated polymerization process is repeated for the generation of the next layer, and so on, until a plurality of superimposed layers forming a desired structure is obtained. In the present method, the structure corresponds to the three-dimensional CAD image. Stereolithography can be performed in the presence of sensitive bioactive molecules. Thus, in accordance with the present invention, prosthetic implants can be built that incorporate drugs.

Stereolithography Instrument

A stereolithography instrument which can be modified and used in the present method is made and sold by 3D Systems, Inc., of Valencia, Calif. under the model name 3D Systems,SLA 250. The instrument comprises a servomechanism which controls the beam of the one or more UV lasers in the X and Y horizontal axis, and a tank for holding the solution comprising the photocurable polymer, photoinitiator, solvent, if necessary, and any other optional components to be incorporated into the prosthetic implant. Located in the tank is a build platform which moves up and down along the Z axis. As modified, the instrument further comprises a build platen for supporting layers of the cross-linked polymer. The build platen, which is situated on the build platform has a plurality of holes that allow the solution to flow therethrough when the platen is lowered and raised during the recoat cycle. However, the initial solid layer of crosslinked polymer must adhere securely to the surface of the build platen to prevent the developing construct from floating freely in the solution which would adversely affect the dimensional and geometric accuracy of the prosthetic implant being built. Specifically, the diameter and pattern of the holes in the build platen is designed such that the construct is not dislodged from the build platen when the table is lowered during the recoat cycle.

Preferably, the UV laser of the stereolithography instrument is tuned to polymerize the primary polymer to a depth of 0.1 mm (100 micron), and thereby to produce solid polymeric layers having a thickness of 0.1 mm, although prosthetic implants whose layers have a thickness greater than or less than 0.1 mm can also be prepared in accordance with the present method.

Solution

The solution comprises chains of at least one photocurable, bioerodable polymer (referred to hereinafter as the "primary" polymer). Although altering the polymer molecular weight of the primary polymer can alter its mechanical properties, including its mechanical strength, it is contemplated that the fracture toughness of certain solid forms of the primary polymer will have a fracture toughness comparable to trabecular bone. Methods of determining the fracture toughness of solid polymers are known in the art. When incubated in a solution that mimics a physiological environment (e.g., phosphate-buffered saline, pH 7.4, 37 C), the solid form of the primary polymer does not produce an acidic spike. In addition, porous photocrosslinked implants formed from the primary polymer biodegrade at a rate which is slow enough to allow for attachment and proliferation of progenitor cells and tissue ingrowth into the implant prior to a significant loss in mechanical strength of the implant A highly preferred primary polymer is poly(propylene fumarate) (PPF). PPF is an unsaturated linear polyester that degrades in the presence of water into propylene glycol and fumaric acid, degradation products that are easily cleared from the human body by normal metabolic processes. The fumarate double bonds in PPF are reactive and can form cross-links. The high mechanical strength and relatively slow degradation rate of cured or cross-linked PPF matrices makes them especially suitable for orthopedic application. Methods of synthesizing PPF are known in the art. For example, a method of synthesizing PPF resins, in general, and PPF resins having a number average molecular weights (Mn) of 2500 and 5000 Da and a polydispersity index of less than 2, in particular, are described in U.S. Pat. No. 6,124,373, which is incorporated herein in its entirety.

Optionally, the solution comprises chains of one or more photocurable polymers other than the primary polymer, referred to hereinafter collectively as "secondary polymers" for preparing a composite prosthetic prosthetic implant. The photocurable secondary polymers may be hydrophilic or hydrophobic. Although not necessary, it is anticipated that the photocrosslinked secondary polymers will be biodegradable.

Preferably, the solution further comprises bioactive molecules. Such bioactive molecules may be encapsulated in a drug delivery system, such as a biodegradable polymeric nanoparticle. Alternatively, the bioactive molecules are linked to the uncured primary polymer either directly or through a hydrophilic spacer such as for example polyethylene glycol (PEG) Methods of making PPF polymer chains that are linked to bioactive molecules without altering the molecular weight distribution of the PPF block are described in U.S. Pat. No. 6,306,821 to Mikos et al which is specifically incorporated herein by reference. In addition, the bioactive molecules may be dispersed in the solution for "entrapment" in the photo-crosslinked regions of the prosthetic implant during the photo-crosslinking process.

Examples of such bioactive molecules include, but are not limited to molecules which promote epitaxial movement of the cells onto the prosthetic implant(e.g., calcium phosphates [CaP], proteins, such as cytokines, that are themselves signals to the cells, proteins belonging to the transforming growth factor superfamily, bone morphogenetic proteins, basic fibroblast factor, platelet derived growth factor, insulin like growth factor, extracellular molecules including osteopontin, ostenectin, osteocalcin, bone sialoprotein, peptides comprising 3 to 30 amino acids, proteoglycans such as hyaluronic acid, and carbohydrates, including starch, cellulose, and chitin.

The solution further comprises at least one photo-initiator having an energy minimum (polymerization threshold) that matches the wavelength and laser energy employed in the method. Optionally, the method employs multiple lasers having different wavelengths and energy. Under these conditions, the solution comprises multiple photoinitiators.

When PPF is used as the primary polymer, it is preferred that the solution further comprise a solvent for decreasing the viscosity of the solution. Preferably, the solvent is non-toxic. The solvent can also be used to uniformly decrease the cross-linking density of the polymeric prosthetic implant and the mechanical strength of the polymeric prosthetic implant Addition of the solvent can also be used to increase the resorption rate of the prosthetic implant. Good results have been obtained using a solution of PPF and a DEF monomer resin as the solvent.

Structure of the SLA Construct and Prosthetic Implant

The prosthetic implant produced by the present method has solid regions comprising a bioerodable solid form of the primary polymer and registered interconnecting pores forming at least one channel, preferably a network of channels, extending from the exterior surface of the prosthetic implant to a predetermined interior region of the prosthetic implant. Such channels permit cell migration of cells and tissue ingrowth into the prosthetic implant. For bone prosthetic implants, it is preferred that the channels have a diameter of from about 100 to 1000 microns.

Following its removal from the stereolithography instrument and prior to its exposure to a post-SLA UV cure, the SLA construct comprises support structures, for example support rods, attached to the lowermost solid polymeric layer of the prosthetic implant. Support structures are highly desirable for supporting all overhangs that cannot be built up from an already supported area only by surface tension of the most recently polymerized material.

The following examples are for illustration only and are not intended to limit the scope of the invention.

EXAMPLE 1

Materials and Methods

The materials used to produce the prosthetic implant were; Poly(propylene fumerate) (PPF) (prepared in the Bioengineering Department, Rice University, Houston, Tex.), Bisacylphosphine Oxide (BAPO) (Irgacure 819) (CIBA Specialty Chemicals Additives Division, Tarrytown, N.Y.), and Chloroform C-295 (Fisher Scientific, Fair Lawn, N.J.). Materials were weighed and mixed in a standard fume cabinet; One gm of BAPO was dissolved in 10 gm of chloroform and mixed thoroughly, 0.5 ml of the BAPO/chl mixture was added to 10 gm of PPF and mixed thoroughly. The resulting resin mixture was poured into a 3½-inch diameter culture dish to a depth of 2 mm.

The stereolithography machine (3D Systems SLA 250, Valencia, Calif.) consists of a servomechanism, which controls the beam of a UV laser in the X and Y horizontal axis, a tank of liquid monomer resin, and a motorized build platform moving in the Z-axis (i.e., vertically up and down in the tank of resin). A build platen is located on the build platform on which the component is built as the laser beam polymerizes the resin one Z-layer at a time. A 3D model of the prototype component to be manufactured was designed using a computer-aided-design software package (Pro/ENGINEER 2000i) and exported as an STL file. The STL file was then imported into the pre-processing software of the 3D Systems SLA 250 machine (Maestro). The 3D model volume was split in Z-axis into 0.004 inch horizontal slices; the X-axis and Y-axis profile data of each slice controls the focus point of the UV laser beam as it traces out the slice profile. The UV laser cross-links or polymerizes the resin at the point of focus and produces a solid representation of the model at that particular Z-axis location.

The build of the PPF component was carried out in a 3½-inch diameter culture dish that served to act as a build sub-tank to minimize the volume of material required and to prevent contamination of the PPF from the standard acrylic resin. To carry out the build, a custom fixture was screwed to the build platen and the build sub-tank locked in place on the fixture. The PPF and photo-initiator mixture was poured into the dish to a depth of 2 mm. The build platen was then loaded on to the build platform of the SLA machine. Prior to starting the build it the level of the PPF in the sub-tank was calibrated relative to the resin level in the standard build tank to ensure that the laser beam focused at the correct Z-depth prior to starting the build.

The support structures, which normally precede the first Z-slice proper of the component, were eliminated. The lack of support structures limited the number of Z-slices built because without the supports the solid component produced by each lased slice would be free to 'float' within the liquid polymer.

Results and Discussion

The results demonstrated that a solid polymeric PPP device could be successfully manufactured using the sterelithographic rapid prototyping process by cross-linking the biocompatible, biodegradable polymeric material, (polypropylene fumerate) (PPF) mixed with a suitable photo-initiator (bisacylphosphine oxide) (BAPO) and UV laser light (325 nm wavelength).

The prototype component build was only four Z-slices thick (0.016 inch) due to the limitation of the set-up. It was found that each Z-slice lost its registration with the preceding slice as a result of it floating freely in the liquid resin. Although registration was lost, the slices formed a solid component. Thus, there was cross-linking between the slices in addition to cross-linking with the two slices. The loss of registration between slices was expected and was a result of not including support structures in the built CAD file. Support structures are desirable to promote inter-slice registration and to prevent any overhanging surfaces from collapsing into the vat prior to their joining the rest of the object that is being generated.

These results indicate that internal porosity of the polymeric prosthetic implant should be controllable using the present method. Controlled porosity would allow communication of any desired spaces. This control over prosthetic implant internal geometry allows construction of custom designed prosthetic prosthetic implants with complex internal a structures suitable for optimal stem cell, growth factor, vascular promotion factor, and immunological management factor seeding, as well as desired host cell recruitment, which together promote maturation of cells to adult tissue configurations and prosthetic implant resorption.

EXAMPLE 2

Materials and Methods

The materials used to prepare the device were; Poly (propylene fumarate) (PPF) (Rice University-Bioengineering Department, Houston, Tex.), Diethyl fumarate (DEF) solvent, (Fisher Scientific, Fairlawn, N.J.), Bisacylphosphine Oxide (BAPO) photoiniator (Irgacure 819) (CIBA Speciality Chemicals Additives Division, Tarrytown, N.Y.). Materials were weighed and mixed in a standard fume cabinet. Two grams of BAPO were dissolved in 200 g of DEF and mixed thoroughly. The BAPO/DEF mixture was then added to 280 g of PPF and mixed thoroughly. The quantities of DEF and PPF used resulted in a mixture that had similar viscosity properties to the native resin normally used with the SLA machine. The DEF/PPF resin was allowed to stand for 30 minutes to allow air bubbles trapped in the mixture to dissipate.

Method

The stereolithography machine used was an SLA 250/40 (3D Systems Valencia, Calif.). The SLA 250/40 consists of a servomechanism, which controls the beam of a UV laser in the X and Y horizontal axis, a tank containing a liquid monomer resin, and a motorized build platform that is controlled in the Z-axis (FIG. 1). The build platform is located so that it travels vertically up and down in the tank of resin. A build table is located on the build platform on which the part is built as the laser beam polymerises the resin one Z-layer at a time.

Figure 2:
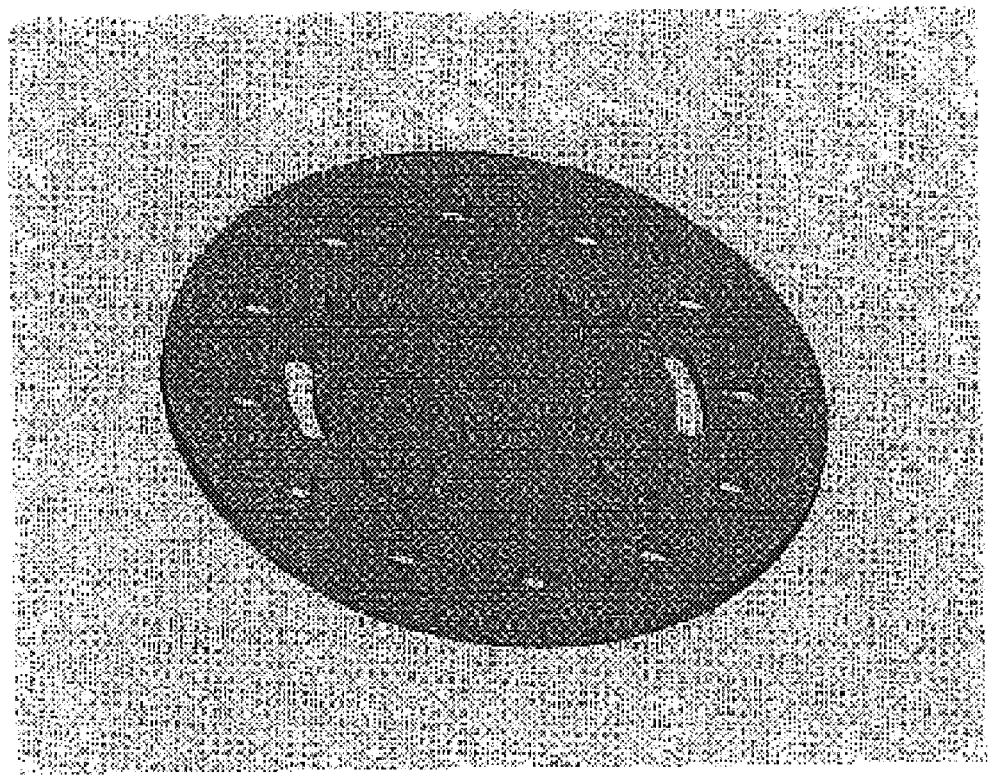
FIG. 2: Pro/ENGINEER rendered CAD image of prototype PPF construct: The series of slots and projections test the inter-slice PPF registration. Overall dimensions are 50 mm diameter×4 mm thick.

A 3D model of the prototype part to be manufactured (FIG. 2) was designed using a 3D solid modelling computer-aided-design (CAD) software package, Pro/ENGINEER 2000i$^2$ (PTC, Needham, Mass.), and exported as an STL file. The STL file was imported into the pre-processing software, Maestro (3D Systems Valencia, Calif.), on the 3D Systems SLA 250/40 console and was used to control the laser in the X-Y plane and the table in the Z-axis. The 3D model volume was split in the Z-axis into 0.1 mm horizontal slices. The X-axis and Y-axis profile data of each slice controls the focal point of the UV laser as it traces the slice profile. The UV laser polymerizes the resin at the focal point and therefore progressively produces a solid representation of the model at that particular Z-slice location.

The manufacture of the PPF/DEF part was carried out in a custom-designed build fixture that incorporated a small build-tank and a build-table driven by the 3D Systems SLA 250/40 elevator. The fixture was designed using Pro/ENGINEER 2000i$^2$ and manufactured in the Engineering Services Workshop at CWRU.

Figure 3:
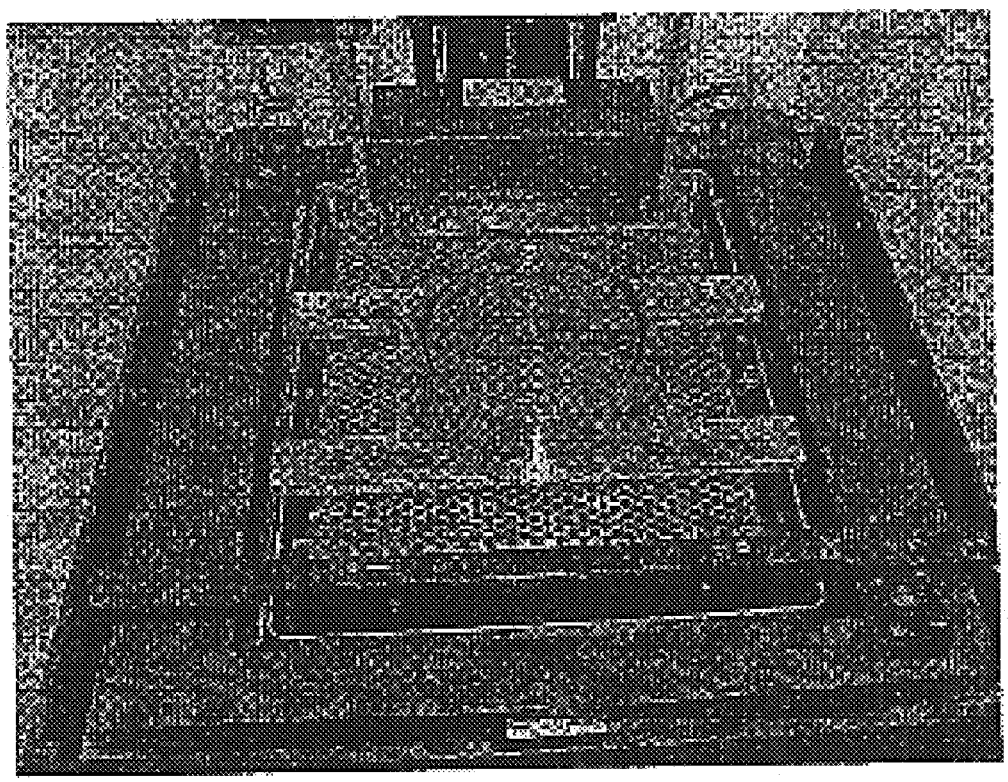
FIG. 3: Custom mini-build tank from above: It is located on the 3D System SLA 250 machine. Note that it takes advantage of the 3D systems elevator hardware but, at this time, not the wiper blade.
Figure 4:
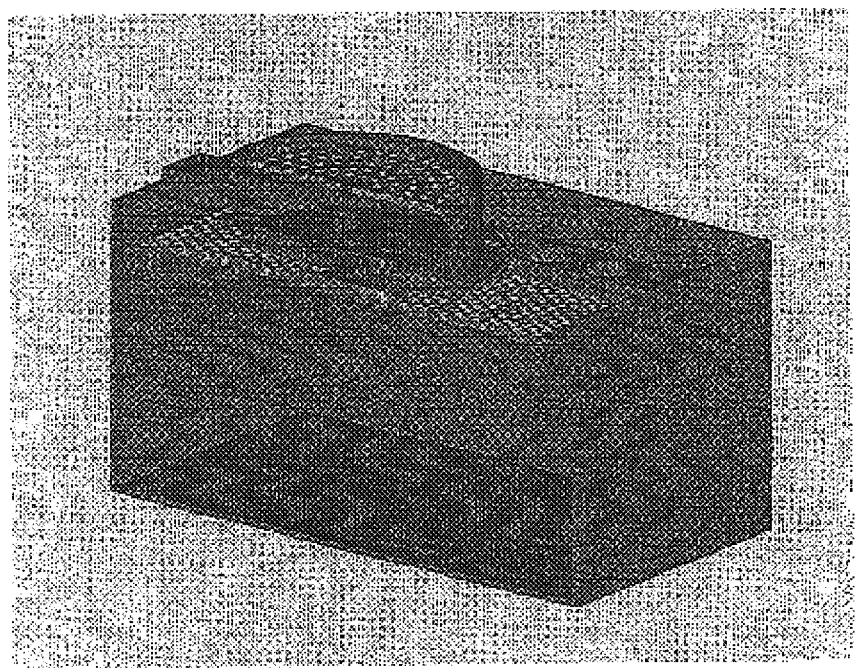
FIG. 4: Custom mini-build tank cross-sectional view: A CAD rendered image showing a section through the custom mini-build tank.

The small build-tank minimized the volume of resin required and also prevented contamination of the PPF/DEF resin from the standard SLA resin. The custom fixture (FIG. 3) was located on the sides of the original build tank and levelled with set-screws to ensure smooth vertical motion of the build-table. The custom build-table was coupled to the SLA 250/40's build-table by means of a small shaft enabling both tables to move in parallel, ensuring the correct Z-axis movement of the custom build-table during the experiment (FIG. 4). The PPF/DEF mixture was poured into the custom build-tank to a depth of 70 mm. Prior to starting the build, the level of the custom build-table was set relative to the PPF/DEF resin in the custom build-tank. This was conducted to ensure that the laser beam was focused at the correct Z-depth prior to starting the build.

The prototype part was designed with features that would test the ability to build solid protrusions (including four circular pads), holes and slots. The overall thickness of the part was 4 mm which would clearly show the ability to cross-link multiple layers and produce a part of a significant and physiologically relevant thickness. The holes and slots would test the ability to reproduce geometric features that could be incorporated into the model to produce controlled porosity.

i. Results

Figure 5:
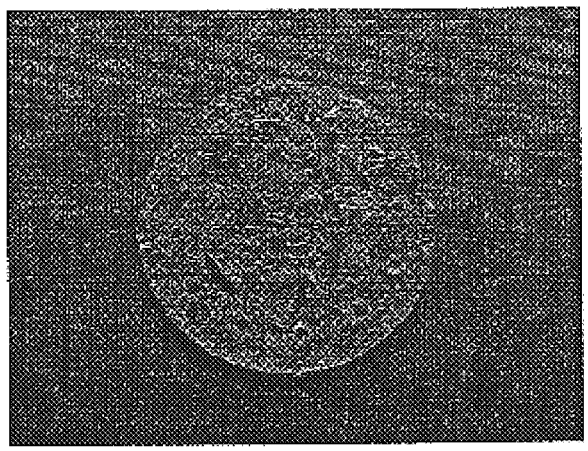
FIG. 5: SLA manufactured PPF/DEF prototype: This part was generated from CAD model data fed to an SLA 250/40. The mottled (dots and lines) on undersurface indicate support structures that were previously attached to the mini-tank build platen.

The PPF/DEF mixture was successfully cross-linked using the stereolithography process described and a multi-layer part was manufactured which closely matched the geometry of the CAD prototype model (FIG. 5). The holes, slots and protrusions showed clearly that registration between layers was maintained. The side faces of the features were vertical and had relatively sharp edges between the vertical and horizontal faces of the top and bottom of the part. The part achieved the total design thickness of 4 mm and was built on supports that were 6.3 mm high, indicating that approximately 80 layers in total were individually crosslinked together. Some of the supports (less than 10%) failed to attach to the build table and the part. Dimpling seen on the resulting part (FIG. 5) is on the underside. These dimples indicate where support structures were attached. After removal from the SLA 250/40 machine, the part was post-cured for 2 hours in a UV enclosure to ensure complete cross-linking of the material.

ii. Discussion

This example successfully demonstrates the feasibility of using the stereolithography process to build and control 3D multi-layer parts made from a biodegradable, biocompatible resin. In the current example; it was a significant achievement to manufacture a part that was of a physiologically relevant size (4 mm maximum thickness and 50 mm diameter) using a commercially available SLA system. These results provide evidence that the present SLA method is a viable process to manufacture large custom scaffolds for tissue engineered prosthetic prosthetic implants.

The differences observed between the CAD model and the SLA fabricated part were mostly due to the limitations of the custom-designed build tank. The custom-designed build tank prevented the resin from being leveled after each recoating cycle with the wiper blade of the SLA machine because the top of the tank was located above the level of the wiper blade. Our initial tests were conducted with high molecular weight, pure PPF that had a high viscosity and surface tension. After each recoat cycle, a convex mound formed over the part surfaces prior to the laser drawing the next slice profile. This resulted in the part having increasingly convex, instead of flat, horizontal surfaces on its upper face. Avoiding this type of "wave" action is the intent of the wiper blade. To minimize the convex-surface effect, a solution of DEF/PPF resin was used. DEF resin has a very low viscosity so by adding this to the pure PPF resin, which has a high viscosity, the viscosity of the resin solution was lowered. Therefore, by controlling the proportions of DEF resin to PPF resin, the viscosity of the solution was controlled to be similar to that of native SLA resin. The convex surface effect can also be minimized by re-engineering the build fixture with a modified design that locates the build tank so that the SLA machine wiper blade is able to conduct its intended function. This modification should allow for parts to be fabricated using higher viscosity DEF/PPF solutions.

What is claimed is:

1. A process for fabricating a customized three-dimensional prosthetic implant, comprising the steps of:
    (a) providing a solution comprising chains of a primary photocurable, bioerodable polymer, a primary photoinitiator for promoting photocrosslinking of the chains of the primary polymer, and a solvent, wherein the primary polymer is poly(propylene fumarate)(PPF);
    (b) providing a stereolithography instrument comprising a primary UV laser for activating the primary photoinitiator and photocrosslinking the PPF chains;
    (c) providing a three dimensional CAD image of a desired three-dimensional prosthetic implant, wherein the three-dimensional CAD image is readable by the stereolithography instrument;
    (d) depositing the solution in successive layers on a build platen in the stereolithography instrument; and
    (e) photocrosslinking at least a portion of the PPF chains in each of the successive layers according to corresponding cross-sectional patterns derived from the three dimensional CAD image to provide a three dimensional construct whose size and external and internal shapes correspond to the three dimensional CAD image.

2. The method of claim 1 wherein the solution comprises chains of a secondary photocurable polymer and wherein the process comprises photocrosslinking PPF chains and chains of the secondary photocurable polymer to provide a composite prosthetic implant.

3. The method of claim 1 wherein the solution comprises chains of a secondary photocurable polymer and a secondary photoinitator for initiating photocrosslinking of the secondary photocurable polymer;

wherein the stereolithography instrument comprises a secondary UV laser for activating the secondary photoinitiator and photocrosslinking the secondary photocurable polymer, wherein the wavelength of radiation emitted by the secondary UV laser is different from the wavelength of radiation emitted by the primary UV laser, and wherein the process comprises photocrosslinking the PPF polymer by activating the primary photoinitiator with the primary UV laser and photocrosslinking the secondary photocurable polymer by activating the secondary photoinitiator with the secondary UV laser to provide a composite prosthetic implant.

4. The process of claim 1 wherein the PPF chains have bioactive molecules attached thereto.

5. The process of claim 1 wherein the three dimensional CAD image has a series of interconnecting pores forming at least one channel leading from the exterior surface of the three dimensional CAD image to a predetermined location in the interior of the three dimensional CAD image, and wherein the construct has a corresponding series of interconnecting pores forming at least one channel leading from the exterior surface of the construct to corresponding location in the interior of the construct.

6. The process of claim 1 wherein the desired three-dimensional CAD image has a network of interconnecting channels, and wherein the construct has a corresponding network of interconnecting channels for promoting attachment of cells and ingrowth of tissue.

7. The process of claim 5 wherein the diameter of the pores is from about 100 to 1000 microns.

8. The process of claim 5 wherein the diameter of the channels is from about 100 to 1000 microns.

9. The process of claim 1 further comprising the steps of washing the construct to substantially remove the solvent and non-crosslinked PPF chains, and exposing the construct to UV radiation to fully cure partially cured regions of the construct.

10. The process of claim 1 wherein step (a) is preceded by a step comprising scanning a bone to be duplicated to produce data and converting such date into the three dimensional CAD image.

11. The process of claim 10 wherein said scanning is three dimensional CT scanning.

12. The process of claim 1 wherein the solvent is non-toxic.

13. The process of claim 1 wherein the solvent comprises diethyl fumarate.

14. The process of claim 1, wherein select cross-linked regions of the layers of the construct are offset to form a porous network.

15. The process of claim 1 wherein the UV laser of the stereolithography instrument is tuned to polymerize the primary polymer to a depth of 0.1 mm (100 micron), and to produce solid polymeric layers having a thickness of 0.1 mm.

* * * * *